United States Patent [19]

Laly et al.

[11] Patent Number: 5,514,383
[45] Date of Patent: May 7, 1996

[54] PROCESS FOR THE PREPARATION OF TABLETS OF DERIVATIVES OF CEPHALOSPORANIC ACID BY DIRECT COMPRESSION

[75] Inventors: Jean-Louis Laly, Tours; Roberto Lombardi, Saint Germain en Laye, both of France

[73] Assignee: Rhone-Poulenc Rorer S.A., Cedex, France

[21] Appl. No.: 64,049

[22] PCT Filed: Nov. 8, 1991

[86] PCT No.: PCT/FR91/00872

§ 371 Date: May 14, 1993

§ 102(e) Date: May 14, 1993

[87] PCT Pub. No.: WO92/00463

PCT Pub. Date: May 29, 1992

[30] Foreign Application Priority Data

Nov. 15, 1990 [FR] France .................. 90 14210

[51] Int. Cl.[6] ........................... A61K 9/20
[52] U.S. Cl. ................. 424/464; 424/489; 424/470
[58] Field of Search .................... 424/470, 489, 424/464, 246; 514/202, 210

[56] References Cited

U.S. PATENT DOCUMENTS

| | | | |
|---|---|---|---|
| 4,015,000 | 3/1977 | Kocsis et al. | 424/246 |
| 4,708,956 | 11/1987 | Hirata et al. | 514/210 |
| 5,151,417 | 9/1992 | Sasho et al. | 514/202 |

OTHER PUBLICATIONS

Chemical Abstracts, vol. 112, No. 4, Abstract No. 25681s, Jun. 12, 1989, Ono Tomoi, Antiulcer agents containing cefixime (salts) English Abstract.

Chemical Abstracts, vol. 109, No. 12, Abstract No. 98626a, Jun. 28, 1988, Antibiotic drugs; cefixime trihydrate; cefixime trihydrate tablets and cefixime trihydrate powder for oral suspension English Abstract.

Derwent, Accession No. 89-327676, Sep. 27, 1989, 2-cephem cpds. having vinyl gp. at 3-position-useful as antibacterial agents effective against Gram-positive and English Abstract.

*Primary Examiner*—Thurman K. Page
*Assistant Examiner*—William E. Benston, Jr.
*Attorney, Agent, or Firm*—Ross J. Oehler

[57] ABSTRACT

The present invention relates to a pharmaceutical form based on cephalosporin. It relates in particular to a tabletted pharmaceutical form.

7 Claims, 1 Drawing Sheet

HARDNESS = f (UP FORCE)

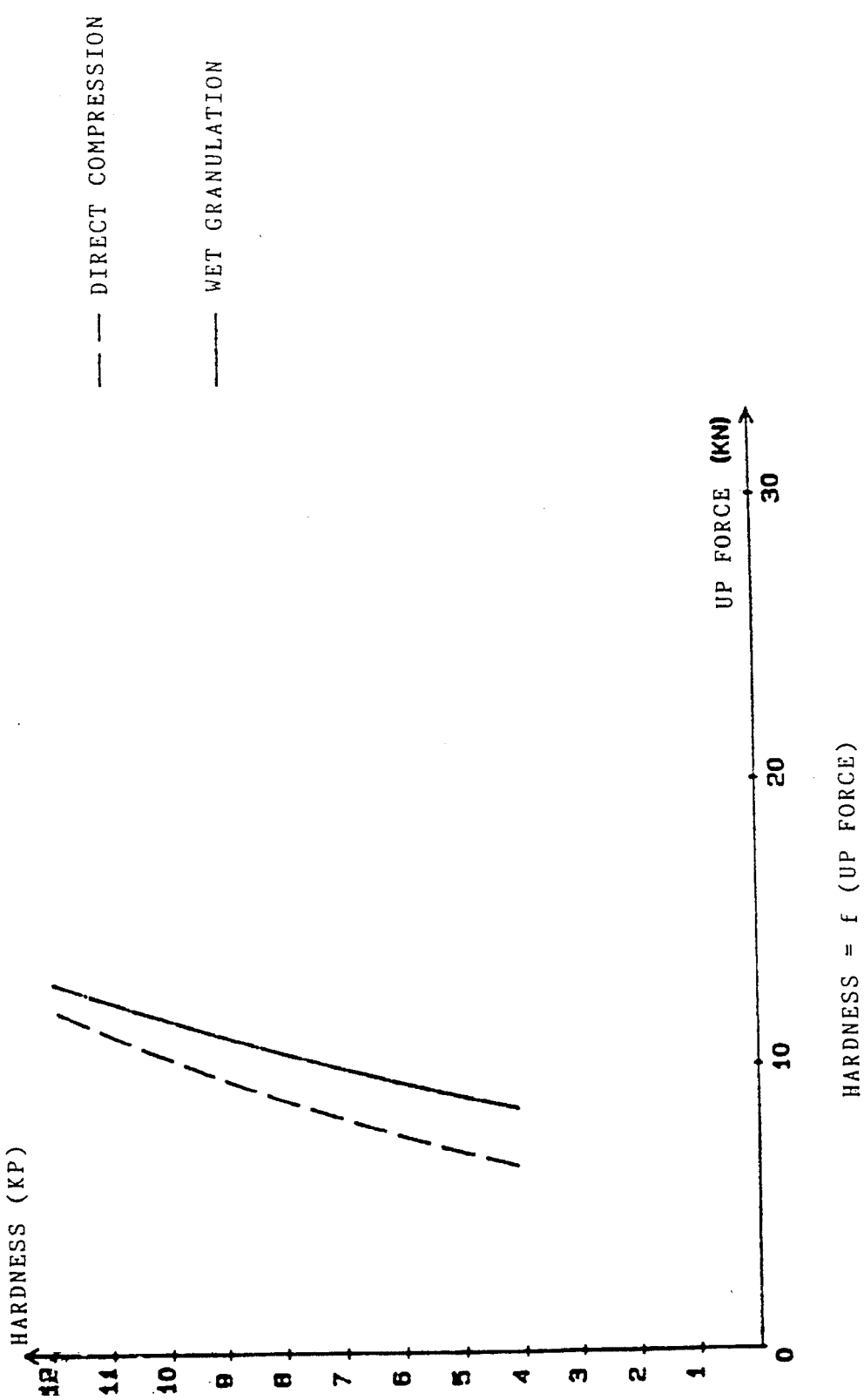
FIGURE 1/1

PROCESS FOR THE PREPARATION OF TABLETS OF DERIVATIVES OF CEPHALOSPORANIC ACID BY DIRECT COMPRESSION

The present invention relates to a new pharmaceutical form based on cephalosporin. It relates more particularly to a new tabletted pharmaceutical form.

The invention relates very particularly to a new tabletted pharmaceutical form based on a semi-synthetic derivative of 7-acylaminocephalosporanic acid which can be administered orally. It relates preferably to the derivatives of 7-acylamino-3-vinylcephalosporanic acid. It relates above all to the forming of (6R,7R)-7-[(Z)-2-(2-amino-4-thiazolyl)-2-carbomethoxyiminoacetamido] -8-oxo-3-vinyl-5-thia-1-aza-2-bicyclo[ 4.2.0]octene-2-carboxylic acid. This cephalosporin is better known under the international common name of Cefixime.

The compounds of the cephalosporin class exhibit a high antibiotic activity; their use is reserved, furthermore, to relatively severe cases when another antibiotic therapy has turned out to be unsatisfactory. These compounds from [sic] their very high activity have led some countries to create very strict legislation relating to their production. Thus, compounds of this kind may be manufactured and formed only in specific rooms, this being in order to avoid any cross-contamination with any other medication.

Another difficulty in the forming of these active substances is due to their cost. Indeed, these products are obtained by a lengthy process requiring a large number of stages of synthesis and are therefore offered, when purchased, at an extremely high material cost.

It is therefore indispensable, for the two reasons referred to above, to have a processing technique which avoids product losses as much as possible.

Insofar as the techniques of pharmaceutical forming into tablets are concerned, two preparative routes are known:

forming by a wet route forming by direct compression.

In the first case, that is to say in the case of forming of active substances by a wet route, the following series of stages should be envisaged:

weighing the active substances and excipients delumping and screening the various constituents of the final formulation primary mixing of the active substance and of the excipients and checking the homogeneity of the mixture obtained wetting of the mixture granulation drying grading of the particles dilution final mixing compression.

This series of stages requires the presence of eight different types of apparatus. Because of the toxicity of the active substance, the whole of the forming operation requires spotless cleaning in the case of each of these pieces of equipment. The changing of equipment on the one hand increases the cost of production significantly, since the losses cannot be reduced to a value of less than 2% and, on the other hand, prevents any automation of the process. Environmental protection and industrial hygiene are proportionally more difficult to control, the higher the number of stage of synthesis and of pieces of equipment. The wet route process additionally requires a drying stage with a risk of deterioration of the product which is far from being negligible. All these technical constraints, plus the legislative constraints with regard to the environment, have led industrialists to abandon forming by a wet route.

The second possible route for preparing a tabletted pharmaceutical form of an active substance consists in carrying out a direct compression of a mixture of powders, a mixture which in the case of the present invention consists of the cephalosporin and excipients.

It appeared that this technique was also to be proscribed within the scope of the present invention, in view of the high proportion of the active substance in relation to excipients. The direct compression process applies generally to tablets in which the quantity of active substance is smaller than 100 mg and in which the proportion of the active substance in the tablet does not exceed 25%. Above this percentage it is impossible to "bury" the active substance in the mass of the excipients and thus to be free from the physical and chemical constraints on the active substance.

Quite astonishingly it has been found that within the scope of the present invention all these problems have been solved by carrying out a direct compression of a mixture containing a cephalosporin and one or more excipients in a weight proportion of the active substance in the tablet ranging between 20 and 90% and preferably between 30 and 70%.

The cephalosporin employed in the present invention is preferably a derivative of 7-acylamino- 3-vinylcephalosporanic acid and most particularly the said derivative is that marketed under the name of Cefixime.

The excipients used are chosen especially from:

calcium carbonates calcium phosphates calcium sulphates microcrystalline celluloses cellulose powders fructoses the various forms of lactose mannitols sorbitols starches pregelled starches sugars.

Lubricating agents may also be added, such as magnesium stearate, stearic acid, talc or a polyethylene glycol.

The particle size distribution of the active substance which is preferred for implementing the compression by a dry route of the present invention is the following:

fewer than 5% of particles larger than 250 μm between 55 and 95% of particles between 250 and 90 μm between 5 and 40% of particles smaller than 90 μm.

The relative density of the active substance is preferably between 0.6 and 0.9.

The process of preparation consists in weighing the various constituents, delumping them and carrying out a first mixing with all the constituents but without the lubricating agent, and then the lubricating agent is added, the final mixing is carried out and the compression is performed. This process employs only four pieces of equipment, and this brings the advantage of reducing the losses of active substance to below 1%.

The tablets obtained by the process described above, which also form part of the invention, exhibit a friability and cleavage criteria which are better than the same tablets manufactured by a wet-route compression. They exhibit an excellent uniformity of distribution of the active substance.

The invention will be described more completely with the aid of the following examples, which should not be considered as limiting the invention.

EXAMPLE 1

The following substances are used:

| Cefixime trihydrate | 184.60 kg |
|---|---|
| Pregelled starch (Starch 1500) | 48.98 kg |
| Dicalcium phosphate dihydrate | 122.44 kg |
| Magnesium stearate | 2.03 kg |
| Microcrystalline cellulose (Avicel PH 102) | 41.95 kg |

The Cefixime trihydrate has the following particle size distribution:

The various substances, active substance and excipient are passed through a screen with a 1-mm mesh to carry out a delumping operation.

The substances are weighed and charged—except for the magnesium stearate—into a 1,000-liter mixer. Mixing is carried out for 10 minutes at a speed of 10 revolutions per minute.

The magnesium stearate, delumped beforehand on a 0.680-mm screen, is added. Mixing is again carried out for 5 minutes.

A Fette P 2000 press with a station number of 43 is employed for compressing. 200,000 tablets per hour are produced. The weight of tablets manufactured is 397 kg, which represents a production efficiency of 99.2%. The tablets have a mean weight of 491.5 mg with a scatter in accordance with the French Pharmacopoeia. The determination of Cefixime performed on 15 tablets varies from 192.7 mg to 200.8 mg.

The hardness of the tablets was measured on 20 tablets in the conventional manner on an apparatus of the Schleuniger 4M type; the measurement gives 100 to 140 newtons.

The pressability of the mixture was also measured as a function of the force applied to the upper punch (expressed in kilonewtons) on an extensometry line using a set of sensors which measure the deformation of the upper and lower punches and the movement of the upper punch in the matrix of the compression machine. Comparative curves expressing the pressability of the mixture were established. These curves result from the measurement of the hardness of the tablets in a Schleuniger apparatus as a function of the force, in newtons, applied to the upper punch. This force is measured with a strain gauge. Comparative extensometry curves were established for tablets obtained by wet compression and by direct compression (see FIG. 1). The curve obtained shows that simple mixing offers a better response to compression. The tablets obtained by direct compression exhibit a hardness which is markedly higher than those obtained by wet granulometry.

The various materials, active substance and excipient are passed through a grid screen with a mesh opening of 0.8 mm to carry out a delumping operation.

The materials are weighed and charged—except for the magnesium stearate—into a 150-liter mixer. Mixing is carried out for 10 minutes at a speed of 10 revolutions per minute. The magnesium stearate, delumped beforehand on a 0.650-mm screen, is added. Mixing is again carried out for 5 minutes.

A Courtoy R 100 press with a station number of 24 is employed for compressing. 110,000 tablets per hour are produced.

The tablets have a mean weight of 596.3 mg with a scatter in accordance with the French Pharmacopoeia. The determination of Cefixime performed on 20 tablets varies from 394.4 mg to 407.12 mg. The hardness of the tablets measured with the Schleuniger apparatus on 20 tablets varies from 100 to 140N.

Comparative Example 1

The following materials are used:

| Cefixime trihydrate | 106.620 kg |
|---|---|
| Pregelled starch (Starch 1500) | 6.750 kg |
| Dicalcium phosphate dihydrate | 2.700 kg |
| Microcrystalline cellulose (Avicel PH 102) | 7.868 kg |

The starting materials are weighed, screened and then charged into a 400-liter mixer-granulator. Dry mixing is carried out for 5 minutes. 24 kg of water are then added and then 8.32 kg of water are added gradually until a granulated mass which contains 27% of water is obtained. The granulation takes 7 minutes.

The granules are then dried in a fluidised air bed drier for 1 hour 15 minutes with an air entry temperature of 45° C. and an exit temperature of 18° C.–25° C. The granulate obtained is then passed over a screen with a mesh size of 1 mm. 119.938 kg of granules are obtained.

The following are then weighed:

| Microcrystalline cellulose | 14.394 kg |
|---|---|
| Pregelled starch | 19.948 kg |
| Dicalcium phosphate dihydrate | 63.838 kg |
| Magnesium stearate | 0.886 kg |

The granules obtained previously are mixed with the cellulose, starch and phosphate, the stearate is then added and 217.550 kg of final product are obtained. This mixture is compressed in a Fette P 2000 press. A mass of tablets of 215.38 kg is obtained, which represents a yield of 98% based on the mass employed. The tablets have a unit weight of 490 mg and an extensometry curve as shown in the diagram of FIG. 1. The friability of the tablets, measured by the TAB method at 10 minutes is 0.3%. The hardness of the tablets varies from 85 to 95N.

We claim:

1. A dry process for the preparation of tablets of 7-acylaminocephalosporanic acid comprising carrying out a direct compression of a mixture comprising said acid and at least one pharmaceutical excipient, said acid comprising at least about 25% by weight of said mixture and wherein the 7-acylaminocephalosporanic acid has a particle size distribution such that:

fewer than 5% of particles have a diameter greater than 250μ, between 55 and 95% of the particles have a diameter of between 250 and 90μN, and between 5 and 40% of the particles have a diameter smaller than 90μ.

2. Process of preparation according to claim 1, wherein the mixture employed for the direct compression contains 30 to 70% by weight of the said acid relative to the weight of the final tablet.

3. Process according to claim 1, wherein the 7-acylaminocephalosporanic acid has a relative density of between 0.6 and 0.9.

4. Process according to claim 1, wherein the 7-acylaminocephalosporanic acid derivative is a derivative of 7-acylamino-3-vinylcephalosporanic acid.

5. A process according to claim 1, wherein the excipients are selected from the group consisting of calcium carbonates, calcium phosphates, calcium sulphates, microcrystalline celluloses, cellulose powders, fructoses lactoses, mannitols, sorbitols, starches, pregelled starches and sugars.

6. Process according to claim 5, wherein a lubricating agent chosen from magnesium stearate, stearic acid, talc and a polyethylene glycol is added.

7. Tablets of derivatives of 7-acylaminocephalosporanic acid prepared using the process according to claim 1.

* * * * *